(12) United States Patent
Senior (10) Patent No.: US 10,426,595 B2
(45) Date of Patent: Oct. 1, 2019

(54) ELONGATE GUIDE ELEMENT FOR AN IMPLANT

(71) Applicant: Xiros Limited, Leeds, Yorkshire (GB)

(72) Inventor: Martin Russell Senior, Wetherby (GB)

(73) Assignee: XIROS LIMITED, Leeds, Yorkshire (GB)

( * ) Notice: Subject to any disclaimer, the term of this patent is extended or adjusted under 35 U.S.C. 154(b) by 0 days.

(21) Appl. No.: 14/919,502

(22) Filed: Oct. 21, 2015

(65) Prior Publication Data

US 2016/0113755 A1   Apr. 28, 2016

(30) Foreign Application Priority Data

Oct. 22, 2014 (GB) .................................. 1418760.3

(51) Int. Cl.
*A61B 17/04* (2006.01)
*A61F 2/08* (2006.01)

(52) U.S. Cl.
CPC ........ *A61F 2/0805* (2013.01); *A61B 17/0401* (2013.01); *A61F 2/0811* (2013.01);
(Continued)

(58) Field of Classification Search
CPC ........ A61B 17/0401; A61B 2017/0406; A61B 2017/0404
See application file for complete search history.

(56) References Cited

U.S. PATENT DOCUMENTS 4,773,910 A   9/1988   Chen et al.
5,013,292 A   5/1991   Lemay
(Continued)

FOREIGN PATENT DOCUMENTS

EP   1889575 B1   12/2009
JP   2001198147 A   7/2001
(Continued)

OTHER PUBLICATIONS

German, Randall M., "Progress in Titanium Metal Powder Injection Molding," Materials, Aug. 20, 2013, 6, 3641-3662, DOI: 10.3390/ma6083641, XP055235597, http://www.mdpi.com/1996-1944/6/8/3641, 22 pgs.
(Continued)

*Primary Examiner* — Brian E Pellegrino
(74) *Attorney, Agent, or Firm* — Stoel Rives LLP (57) ABSTRACT

The invention relates to an elongate guide element (22) for guiding an implant (1) along a tunnel (17) in a bone (12, 14) and for securing the implant within the tunnel. One exemplary guide element comprises: first end and second ends (24, 26); a pair of support apertures (42) for receiving a support element (3) for the implant, the support apertures being spaced apart in a direction along a main longitudinal axis (28); a saddle (46) extending transverse to the longitudinal axis, one of the pair of support apertures being disposed between the saddle and the first end and the other between the saddle and the second end. The support element extends through one of the pair of support apertures, at least partly around the saddle and then through the other aperture. The guide element has a generally planar bone facing surface (48) and a second opposite surface (50). The guide element has a height, measured in a direction from the planar surface towards the second surface, the height increasing in a direction from the first and second ends towards an intermediate section of maximum height (H). At least part of the saddle is disposed within the intermediate section and defines a space (54) between the second surface and a maximum height extent of the saddle, for receiving part of the support element.

24 Claims, 4 Drawing Sheets

(52) U.S. Cl.
CPC .............. *A61B 2017/0404* (2013.01); *A61F 2002/0852* (2013.01); *A61F 2002/0882* (2013.01)

(56) References Cited

U.S. PATENT DOCUMENTS

| | | | |
|---|---|---|---|
| 5,306,301 A | 4/1994 | Graf et al. |
| 5,693,060 A | 12/1997 | Martin |
| 6,099,568 A | 8/2000 | Simonian et al. |
| 6,110,207 A | 8/2000 | Eichhorn et al. |
| 6,117,161 A | 9/2000 | Li et al. |
| 7,097,654 B1 | 8/2006 | Freedland |
| 7,530,990 B2 | 5/2009 | Perriello et al. |
| 7,662,161 B2 | 2/2010 | Briganti et al. |
| 8,007,533 B2 | 8/2011 | Zhukauskas et al. |
| 8,323,338 B2 | 12/2012 | LeBeau et al. |
| 8,535,377 B2 | 9/2013 | Myers et al. |
| 8,617,241 B2 | 12/2013 | Myers |
| 8,702,796 B2 | 4/2014 | Myers |
| 8,834,523 B2 | 9/2014 | Ferragamo et al. |
| 8,920,463 B2 | 12/2014 | McGuckin, Jr. et al. |
| 8,926,662 B2 | 1/2015 | Perriello et al. |
| 9,028,547 B2 | 5/2015 | Lebeau et al. |
| 9,056,003 B2 | 6/2015 | Demmer et al. |
| 2002/0161439 A1 | 10/2002 | Strobel et al. |
| 2005/0033363 A1 | 2/2005 | Bojarksi et al. |
| 2006/0190041 A1 | 8/2006 | Fallin et al. |
| 2006/0229722 A1 | 10/2006 | Bianchi et al. |
| 2006/0285991 A1 | 12/2006 | McKinley |
| 2007/0162125 A1* | 7/2007 | LeBeau .............. A61B 17/0401 623/13.14 |
| 2007/0233241 A1 | 10/2007 | Graf |
| 2007/0270857 A1 | 11/2007 | Lombardo |
| 2008/0046009 A1 | 2/2008 | Albertorio et al. |
| 2008/0082128 A1 | 4/2008 | Stone |
| 2010/0324676 A1 | 12/2010 | Albertorio et al. |
| 2011/0029013 A1* | 2/2011 | McGuckin ......... A61B 17/0401 606/213 |
| 2011/0213415 A1 | 9/2011 | McGuckin, Jr. et al. |
| 2012/0059416 A1 | 3/2012 | Justin et al. |
| 2012/0109194 A1 | 5/2012 | Miller et al. |
| 2013/0085568 A1 | 4/2013 | Smith et al. |
| 2014/0155937 A1 | 6/2014 | Shinde |
| 2014/0214163 A1 | 7/2014 | Demmer et al. |

FOREIGN PATENT DOCUMENTS

| | | |
|---|---|---|
| WO | 9720522 A1 | 6/1997 |
| WO | 9812992 A1 | 4/1998 |
| WO | 9947079 A1 | 9/1999 |
| WO | 02091959 A1 | 11/2002 |
| WO | 2007073563 A2 | 6/2007 |
| WO | 2012095868 A2 | 7/2012 |

OTHER PUBLICATIONS

International Search Report and Written Opinion for Serial No. PCT/GB2015/053103 filed Oct. 20, 2015, and mailed from the International Search Authority dated Dec. 21, 2015, 13 pgs.

International Preliminary Report on Patentability for International Application No. PCT/GB2015/053103 filed Oct. 20, 2015, and mailed from the International Preliminary Examination Authority dated Feb. 20, 2017, 7 pgs.

* cited by examiner

ELONGATE GUIDE ELEMENT FOR AN IMPLANT

RELATED APPLICATIONS

This application claims priority to Great Britain Application No. 1418760.3, filed Oct. 22, 2014, which is incorporated by reference in its entirety.

TECHNICAL FIELD

The present invention relates to an elongate guide element for guiding an implant along a tunnel in a bone and for securing the implant within the tunnel, the implant typically comprising a prosthetic ligament or tendon, a tissue graft (such as a harvested tendon of a patient), or a combination thereof. In particular, but not exclusively, the present invention relates to an elongate guide element comprising first and second ends, a main longitudinal axis extending between the ends, and a pair of support apertures for receiving a support element, by which the implant can be coupled to the guide element.

BRIEF DESCRIPTION OF THE DRAWINGS

Embodiments of the present invention will now be described, by way of example only, with reference to the accompanying drawings, in which.

DETAILED DESCRIPTION

Ligament damage, including ACL ruptures, are common in many sports. In the past, one way in which reconstruction of an ACL was carried out was by harvesting two hamstring tendons from a patient, and implanting the tendons in a position where they perform the function of the damaged ACL. However, harvesting two hamstring tendons from the patient seriously limits their residual hamstring function. Conventional reconstruction techniques on other tendons/ligaments suffer from similar problems.

Much research has therefore been carried out into synthetic implants for use generally in the reconstruction of damaged ligaments/tendons in the human body, and one particular area in which a significant amount of research has been carried out is in ACL reconstruction. Elongate textile structures have been used in ACL reconstruction which attach the knee bones (femur and tibia) where a ruptured ACL remains. The elongate structures are intended to bear tensile loading, and may also function as scaffolds that encourage tissue in-growth. The elongate structures are drawn through a tunnel in the bone using an elongate guide element, which is also used to attach the structure to bone. The guide element is provided at one end of the textile structure, and the structure is anchored to bone with a fixation device (such as an interference screw) at its other end.

In one mode of use, the ligament and fixation components are used alone, thereby obviating the need to use additional tissue for the reconstruction, whether autologous (derived from the subject patient) or allogenic (derived from a genetically non-identical donor). In another mode of use, the ligament and fixation components are used in conjunction with a tissue graft, e.g. a single hamstring tendon, which can be suspended from a support element in the form of a loop which is coupled to the guide element, either alongside the ligament or within its tubular structure.

Figure 1A:
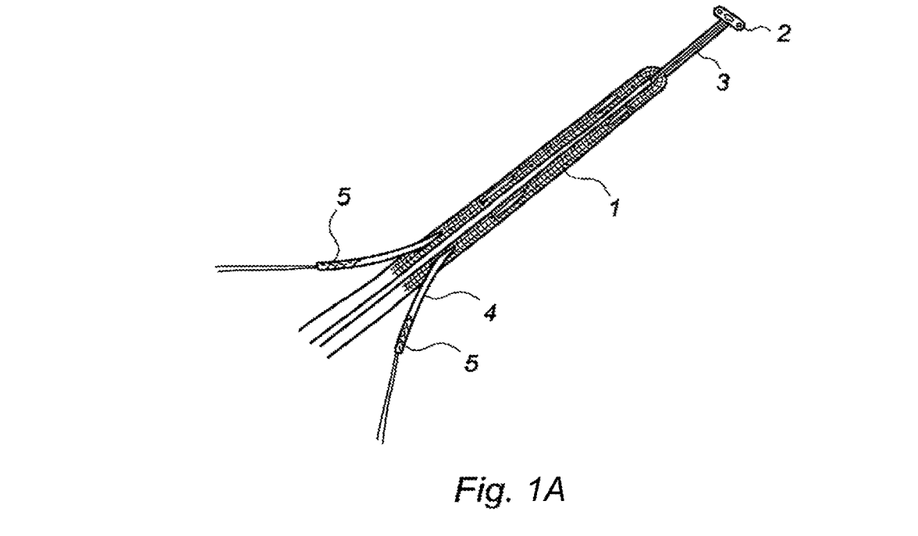
FIG. 1A is a view of a synthetic ligament assembly of a type known in the art and comprising an open weave textile scaffold, guide element, captive continuous loop and a hamstring tendon graft.

The attached drawing Fig. 1A illustrates a prior synthetic ligament assembly comprising a tubular open weave textile scaffold 1, a guide element in the form of an EndoButton™ 2, a support element in the form of a captive continuous loop 3, and a graft 4 comprising a harvested hamstring tendon. The graft 4 has been prepared according to standard procedures, such that each end is whip-stitched with sutures 5 to a length of approximately 35 to 40 mm. The guide element 2 is passed along the length of the bone tunnel, drawing the textile scaffold 1 and graft 4 along the tunnel, and is then 'flipped' to stride the mouth of the tunnel, so that the guide element seats against the external surface of the bone.

This restricts the size of the guide element which can be used, with a relatively small guide element being preferred. However, in at least the early stages of patient rehabilitation, the forces exerted on the guide element following implantation can be very high. This can lead to the (small) guide element fracturing, requiring a complex intervention procedure to be carried out. In addition, small guide elements exert relatively large forces over a small area of bone, which can cause bone resorption.

Increasing the size of the guide element to counteract this is, however, undesirable. This is for two main reasons. Firstly, a larger guide element would necessarily require the drilling of a tunnel of a larger diameter, which presents its own problems. Secondly, for the guide element to stride the tunnel effectively, it would have to be made longer. This would make flipping of the device very difficult, or indeed impossible, without making a skin incision above the tunnel, this being a step which surgeons have managed to avoid by using EndoButton™ type guide elements.

It is therefore amongst the objects of the present invention to obviate or mitigate at least one of the foregoing disadvantages.

According to a first aspect of the present invention, there is provided an elongate guide element for guiding an implant along a tunnel in a bone and for securing the implant within the tunnel, the guide element comprising:

a first end, a second end opposite the first end, and a main longitudinal axis extending between said ends;

a pair of support apertures for receiving a support element by which the implant can be coupled to the guide element, the support apertures being spaced apart in a direction along the main longitudinal axis;

a saddle extending in a direction transverse to the main longitudinal axis, one of the pair of support apertures being disposed between the saddle and the first end and the other between the saddle and the second end, whereby, in use, the support element extends through one of the pair of support apertures, at least partly around the saddle and then through the other one of the pair of support apertures; and a generally planar bone facing surface and a second surface disposed opposite the bone facing surface;

in which the guide element has a height, measured in a direction from the planar bone facing surface towards the second surface, the height increasing in a direction from the first end towards an intermediate section of maximum height disposed between the first and second ends, and in a direction from the second end towards the intermediate section;

and in which at least part of the saddle is disposed within the intermediate section and defines a space between the second surface in the intermediate section and a maximum height extent of the saddle, for receiving part of the support element in order to couple the implant to the guide element.

The guide element may be formed by a metal injection moulding (MIM) process.

According to a second aspect of the present invention, there is provided an elongate guide element for guiding an implant along a tunnel in a bone and for securing the implant within the tunnel, the guide element comprising:

a first end, a second end opposite the first end, and a main longitudinal axis extending between said ends;

a pair of support apertures for receiving a support element by which the implant can be coupled to the guide element, the support apertures being spaced apart in a direction along the main longitudinal axis; and a saddle extending in a direction transverse to the main longitudinal axis, one of the pair of support apertures being disposed between the saddle and the first end and the other between the saddle and the second end, whereby, in use, the support element extends through one of the pair of support apertures, at least partly around the saddle and then through the other one of the pair of support apertures;

in which the guide element is formed by a metal injection moulding (MIM) process.

The elongate guide element of the present invention is of significantly greater strength than prior guide elements of similar dimensions (particularly length and width), especially in the intermediate section of the guide element which supports the greatest loading (imparted on the guide element by the implant, via the support element).

In the guide element of the first aspect of the invention, the improvement in strength may be due to the increased height of the element in the intermediate section, which experiences the greatest loading. Significantly, this is achieved in a manner which restricts difficulties that could otherwise occur during implantation, in particular passage of the guide element along the bone tunnel due to the increased height of the intermediate section. This is because the height increases in directions from the first and second ends towards the intermediate section. The increase in height may therefore be progressive, which may define a relatively smooth transition towards the maximum height intermediate section.

In the guide element of the second aspect of the invention (and of the first aspect where formed in an MIM process), the/an improvement in strength may be achieved by forming the guide element in an MIM process. The guide element may be formed from a feedstock material comprising a metal and a plastics binder. The feedstock material may be formed by mixing a powdered or granular metal material and a plastics binder material and then forming the mixture into pellets. Suitable metal materials include Titanium and alloys thereof. Suitable plastics materials include thermoplastics materials. The pelletised feedstock material may be heated to melt the plastics binder; injected into a mould to form a guide element of generally desired dimensions; cooled and ejected from the mould; subjected to a debinding process in which a portion of the plastics binder is removed (e.g. by solvent extraction or catalytic decomposition); and the de-bounded element then sintered to decompose any remaining binder material and densify the guide element. Optionally the sintered guide element may be hot isostatically pressed (HIP'd) to achieve a desired density in the finished guide element. A finishing procedure may then be carried out which may include machining, surface finish enhancing and/or other suitable procedures.

The space defined between the second surface and a maximum extent of the saddle may receive said part of the support element, so that the support element is effectively located in a recess in the second surface of the guide element. This may: restrict the likelihood of the support element suffering damage during passage along the bone tunnel; reduce the likelihood of the guide element becoming lodged in the tunnel by contact between the support element and a wall of the tunnel; and/or enable use of a support element of larger dimensions (particularly width) than might otherwise be the case. On the latter point, this may be advantageous because it may avoid a requirement to use a higher strength, higher cost material for the support element (the aim there being to provide a support element of smaller dimension e.g. width).

The maximum extent of the saddle may be considered in the direction that the height of the guide element is measured. Accordingly, the maximum extent of the saddle may be a maximum height. An opposite (minimum) extent of the saddle may be disposed in the plane of the generally planar bone facing surface. The saddle may therefore extend from the planar surface towards the second surface. A portion of the saddle disposed in said plane may be generally planar. Alternatively, a space may be defined between the bone facing surface in the intermediate section and a minimum extent of the saddle.

The saddle may have a surface which defines the upper extent of the saddle, and said surface may be generally curved. The surface may be curved in a direction along the longitudinal axis of the guide element. The surface may have a constant radius of curvature. Alternatively, the surface may define a planar portion and rounded, curved or radiused edges.

The saddle be disposed substantially perpendicular to the longitudinal axis.

The guide element may comprise a first side wall and a second side wall opposite the first side wall. The side walls may be generally planar, or substantial portions of the walls may be planar. The side walls may extend between the bone facing surface and the second surface. The side walls may increase in height from the first and second ends towards the intermediate section. The height of the guide element may be determined by the heights of the side walls.

The second surface may, in use, be an outer or upper surface of the guide element.

The intermediate section may extend part-way along a length of the guide element. The intermediate section may be disposed substantially centrally along a length of the guide element. The guide element may be symmetrical about a line which is perpendicular to the longitudinal axis and which passes through a midpoint of the element along a length thereof.

The second surface may be generally curved, and may be curved in a direction along the longitudinal axis of the guide element. This may provide a smooth transition from the lower height ends towards the intermediate section, which may facilitate passage of the element along the bone tunnel. A radius of curvature of the second surface may increase in the direction from the first end towards the intermediate section, and from the second end towards the intermediate section. The intermediate section may be of a constant height, so that the second surface is flat (non-curved) in the intermediate section. The radius of curvature may be greatest in the intermediate section and smallest at the first and second ends. Alternatively, the radius of curvature may be substantially constant.

Each support aperture may have a shape which is generally quadrilateral, when viewed in plan and/or taken in a plane which is parallel to the bone facing surface. This may be advantageous in that it may maximise the cross-sectional area of the aperture and thus facilitate positioning of the support element (and optionally other elements/components) in the apertures. Each support aperture may be generally square or generally rectangular in shape. The guide element may define a first side surface of each support aperture and a second side surface opposite the first. The first and second side surfaces may be disposed substantially parallel to the longitudinal axis. The guide element may define a first end surface of each support aperture and a second end surface opposite the first. The first and second end surfaces may be disposed transverse to (optionally substantially perpendicular to) the longitudinal axis. The guide element may define intersection zones or regions between the end surfaces and the side surfaces. At least some (optionally all) of the intersection regions may be curved, rounded or radiused. In this way, the likelihood of the support element being damaged during use, through contact with the guide element, may be reduced. The saddle may define end surfaces of each support aperture. The intersection regions may define a smooth transition between the side surfaces and the end surfaces without defining a hard edge or ridge.

Each support aperture may comprise a first opening which opens on to (or communicates with) the bone facing surface and a second opening, opposite the first, which opens on to (or communicates with) the second surface.

The guide element may define surfaces of the support apertures. The guide element may define intersection zones or regions between the surfaces of the support apertures and the bone facing surface; and/or between the surfaces of the support apertures and the second surface. The guide element may define intersection zones or regions between the end surfaces of the support apertures and the bone facing surface; the end surfaces and the second surface; the side surfaces and the bone facing surface; and/or the side surfaces and the second surface. At least some (optionally all) of the intersection regions may be curved, rounded or radiused. The intersection regions may define a smooth transition between the side/end surfaces of the apertures and the bone facing/second surfaces of the guide element, and so without defining a hard edge or ridge. Again, this may reduce the likelihood of the support element being damaged during use.

The support apertures may each be adapted to receive one of: a pulling element for pulling the guide element through the bone tunnel; and a manipulating element for manipulating the guide element to overlie a mouth of the bone tunnel on emergence therefrom. One of the support apertures may receive the pulling element and the other one the manipulating element. The support apertures may be substantially elongate, to accommodate part of the support element, and part of one of the pulling and manipulating elements. The support apertures may each take the form of a slot.

The guide element may comprise a further aperture, provided towards one of the first and second ends, for receiving one of: a pulling element for pulling the guide element through the bone tunnel; and a manipulating element for manipulating the guide element to overlie a mouth of the bone tunnel on emergence therefrom. One of the support apertures may be adapted to receive part of said other one of the pulling and manipulating elements. The support aperture which receives part of said pulling element/manipulating element may be substantially elongate, to accommodate part of the support element, and part of the respective pulling/manipulating element. The support aperture may take the form of a slot. One of the support apertures may be disposed between the saddle and the further aperture.

The guide element may comprise:

a pulling aperture provided towards one of the first and second ends, the pulling aperture shaped to receive a pulling element for pulling the guide element through the bone tunnel; and a manipulating aperture provided towards the other one of the first and second ends, the manipulating aperture shaped to receive a manipulating element for manipulating the guide element to overlie a mouth of the bone tunnel on emergence therefrom. One of the support apertures may be disposed between the saddle and the pulling aperture, and the other between the saddle and the manipulating aperture.

The further aperture, or the pulling and manipulating apertures, may comprise a first opening which opens on to (or communicates with) the bone facing surface and a second opening, opposite the first, which opens on to (or communicates with) the second surface.

The guide element may define a surface or surfaces of the further aperture, or the pulling and manipulating apertures. The guide element may define intersection zones or regions between the surface(s) of the further aperture, or the pulling and manipulating apertures, and the bone facing surface; and/or between the surface(s) of the further aperture, or the pulling and manipulating apertures, and the second surface. At least some (optionally all) of the intersection regions may be curved, rounded or radiused. The intersection regions may define a smooth transition between the surfaces of the aperture(s) and the bone facing/second surfaces of the guide element, and so without defining a hard edge or ridge. In this way, the likelihood of the pulling/manipulating elements being damaged during use, through contact with the guide element, may be reduced.

The guide element may comprise at least one bridge extending transverse to the longitudinal axis. The bridge may be disposed between the further aperture and one of the support apertures. The guide element may comprise a pair of bridges. One of the bridges may be disposed between (and/or may define) the pulling aperture and one of the support apertures, and the other one of the bridges may be disposed between (and/or may define) the manipulating aperture and the other one of the support apertures. The/each bridge may form an end surface of a respective one of the support apertures, and at least part of a surface of the further aperture, or a respective one of the pulling/manipulating apertures. The bridge may be disposed substantially perpendicular to the longitudinal axis.

The guide element may be elongate in that a length of the element may be greater than other dimensions of the element, in particular a width and a height. Making the guide element elongate facilitates passage of the element along the bone tunnel and manipulation of the element to overlie the tunnel mouth.

According to a third aspect of the present invention, there is provided an assembly for guiding an implant along a tunnel in a bone and for securing the implant within the tunnel, the assembly comprising:

an elongate guide element according to the first or second aspect of the invention;

a pulling element for pulling the guide element through the bone tunnel;

a manipulating element for manipulating the guide element to overlie a mouth of the bone tunnel on emergence therefrom; and a support element by which the implant can be coupled to the guide element.

According to a fourth aspect of the present invention, there is provided an assembly for guiding an implant along a tunnel in a bone and for securing the implant within the tunnel, the assembly comprising:

an elongate guide element according to the first or second aspect of the invention; and a support element by which the implant can be coupled to the guide element, in which the support element comprises Ultra High Molecular Weight Polyethylene (UHMWPE) material.

Optional further features of the assemblies of the third and/or fourth aspects of the invention are as follows.

The assembly may also comprise a pulling element for pulling the guide element through the bone tunnel; and a manipulating element for manipulating the guide element to overlie a mouth of the bone tunnel on emergence therefrom.

The assembly may also comprise an implant. The implant may be or may comprise: a prosthetic ligament; a prosthetic tendon; a tissue graft, which may be autologous (derived from a subject patient) or allogenic (derived from a genetically non-identical donor), and which may be a harvested tendon; and combinations thereof.

The support element may be or may comprise a loop, may comprise a cohesive assembly of twisted filaments, and may be a continuous loop manufactured according to the teachings of International Patent Publication No. WO-99/47079, the disclosure of which is incorporated herein by way of reference. The support element may comprise UHMWPE material.

The pulling element and/or the manipulating element may each be or may comprise a loop. The loop may pass through the respective aperture so that the pulling/manipulating element is secured to the guide element. The pulling element and manipulating element may be multi-filament yarns, or may be mono-filaments.

Further features of the elongate guide element of the third aspect of the invention may be derived from the text set out above relating to the first and/or second aspect of the invention.

Figure 1B:
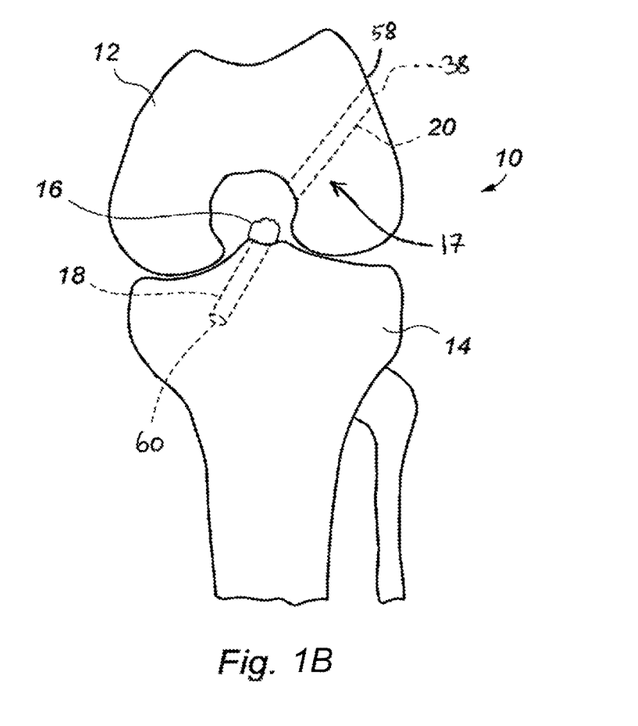
FIG. 1B is a schematic front view of a knee joint between a femur and a tibia of a patient who has suffered ACL rupture, showing the femur and tibia following formation of tunnels in the bones, in preparation for receiving an implant.

Turning firstly to FIG. 1B, there is shown a schematic front view of a knee joint 10 between a femur 12 and a tibia 14 of a patient who has suffered an ACL rupture. A remnant portion of the natural ACL attached to the tibia 14 is shown in the drawing, and given the reference numeral 16. The joint 10 is shown following the formation of a bone tunnel 17 comprising a tunnel portion 18 in the tibia 14 and a tunnel portion 20 in the femur 12, the bone tunnel having been formed following standard procedures which are known in the art. Formation of the bone tunnel 17 is a preparatory step to an ACL reconstruction technique employing synthetic ligament assemblies, in which the present invention has a use, as will now be described.

Figure 2:
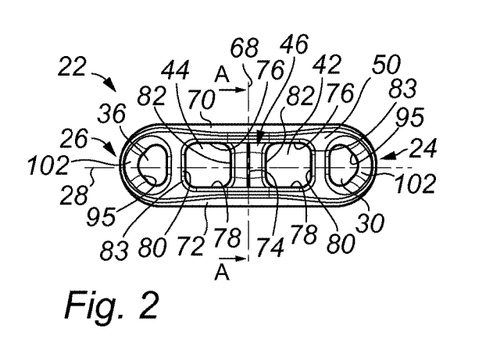
FIGS. 2, 3, 4 and 5 are plan, side, end and bottom views, respectively, of an elongate guide element for guiding an implant along a tunnel in a bone and for securing the implant within the tunnel, in accordance with an embodiment of the present invention.

Accordingly and turning now to FIG. 2, there is shown a plan view of an elongate guide element for guiding an implant along a tunnel in a bone and for securing the implant within the tunnel, the guide element indicated generally by reference numeral 22. The guide element 22 may therefore serve for guiding an implant along the bone tunnel 17 in the joint 10 shown in FIG. 1B. The implant may take any suitable form, and may for example be a prosthetic ligament, prosthetic tendon, tissue graft (which may be autologous or allogenic) such as a harvested tendon, or a combination thereof. The guide element 22 will, however, be described in relation to implantation of an implant in the form of the open weave textile scaffold 1 shown in Fig. 1A, which may or may not comprise the harvested hamstring tendon 5.

Figure 3:
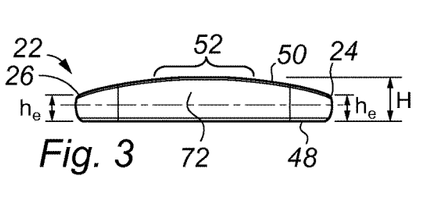
Figure 4:
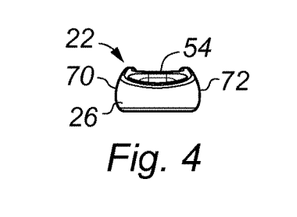
Figure 5:
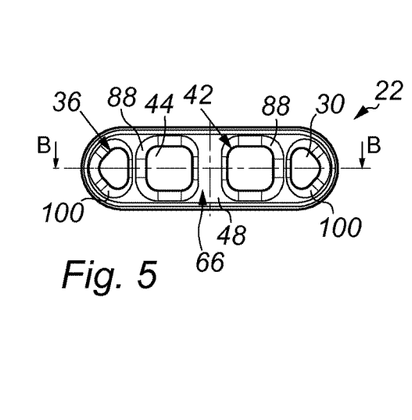
Figure 6:
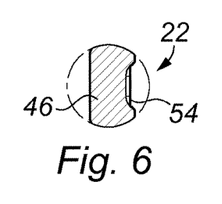
FIG. 6 is an enlarged, cross-sectional detail view of the guide element, taken in the direction of the arrows A-A in FIG. 2.
Figure 7:
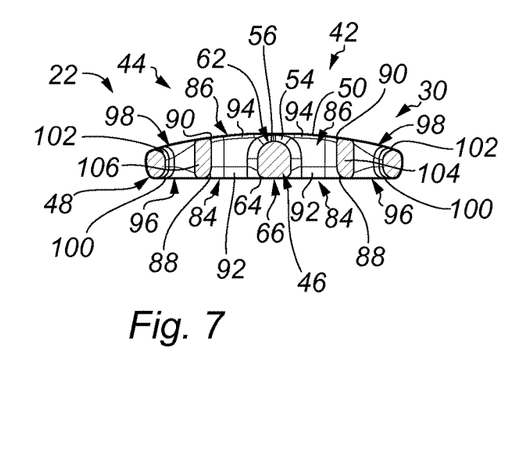
FIG. 7 is a longitudinal cross-sectional view of the guide element, taken in the direction of the arrows B-B in FIG. 5.
Figure 8:
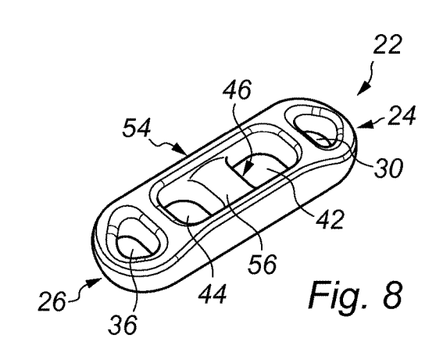
FIGS. 8 and 9 are perspective views of the guide element, taken from above and below, respectively.
Figure 9:
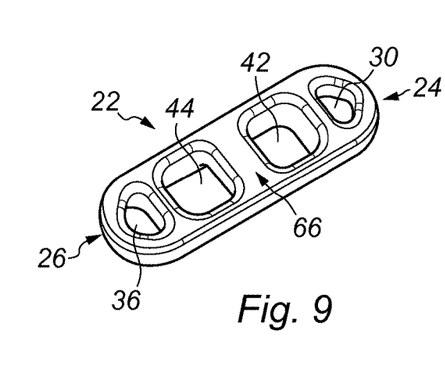

The guide element 22 is also shown in the side, end and bottom views of FIGS. 3, 4 and 5; the enlarged, cross-sectional detail view of FIG. 6, which is taken in the direction of the arrows A-A in FIG. 2; the longitudinal cross-sectional view of FIG. 7, taken in the direction of the arrows B-B of FIG. 5; and the perspective views of FIGS. 8 and 9, taken from above and below, respectively.

The guide element 22 generally comprises a first end 24, a second end 26 opposite the first end, and a main longitudinal axis 28 extending between the first and second ends. Typically the first end 24 will be a leading end and the second end 26 a trailing end, although this will ultimately depend upon the orientation of the guide element 22 within the bone tunnel 17, and the direction in which the guide element is drawn along the tunnel.

Figure 10:
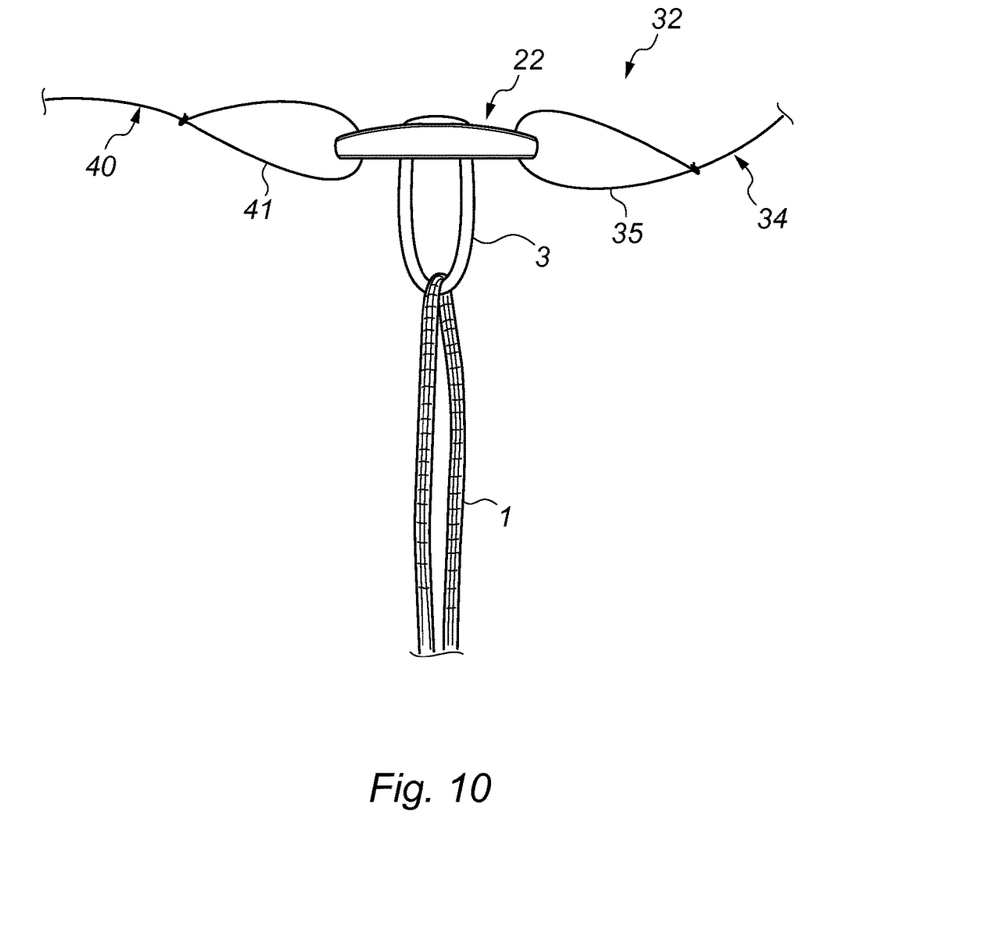
FIG. 10 is a view of an assembly for guiding an implant along a tunnel in a bone and for securing the implant within the tunnel, in accordance with an embodiment of the present invention, and which comprises the guide element of FIGS. 2 to 9.

In the illustrated embodiment, a pulling aperture 30 is provided towards one of the first and second ends 24 and 26, suitably towards the first end 24, and is shaped to receive a pulling element for pulling the guide element through the bone tunnels 18, 20. However and as will be described below, a guide element may be provided without a dedicated pulling aperture. The pulling aperture 30 is provided sufficiently close to the first end 24 so that the guide element 22 orients itself generally parallel to an axis of the bone tunnel 17 during insertion. An assembly for guiding the implant 1 along the bone tunnel 17 and for securing the implant within the tunnel, comprising the elongate guide element 22, is shown in FIG. 10, the assembly indicated generally by reference numeral 32. The pulling element is shown in FIG. 10 and given the reference numeral 34.

The guide element 22 also comprises a manipulating aperture 36 provided towards the other one of the first and second ends 24 and 26, in this case the second end. However and as will be described below, a guide element may be provided without a dedicated manipulating aperture. The manipulating aperture 36 is shaped to receive a manipulating element for manipulating the guide element to overlie a mouth 38 of the bone tunnel 20 (FIG. 1B), the manipulating element being shown in FIG. 10 and indicated by reference numeral 40. The manipulating aperture 36 is provided sufficiently close to the second end 26 so that a force can be exerted on the guide element 22 to flip it.

The guide element 22 also comprises a pair of support apertures 42 and 44 for receiving a support element for the implant. In this case, the support element takes the form of the captive continuous loop 3, the loop and textile scaffold 1 both being shown in FIG. 10. The support apertures 40 and 42 are spaced apart in a direction along the longitudinal axis 28 of the guide element 22, as best shown in FIG. 2. In embodiments which do not comprise a pulling aperture and/or manipulating aperture, one or both of the support apertures may receive either a pulling element or a manipulating element.

The guide element 22 also comprises a saddle 46 extending in a direction transverse to the longitudinal axis 28. One of the pair of support apertures 42 and 40 is disposed between the saddle 46 and the pulling aperture 30, and the other between the saddle and the flipping aperture 36. In the illustrated embodiment, the support aperture 42 is disposed between the saddle 46 and the pulling aperture 30. In use, the loop 3 by which the textile scaffold 1 is coupled to the guide element 22 extends through one of the pair of support apertures 42 and 44, partly around the saddle 46 and then through the other one of the pair of support apertures.

The guide element 22 also comprises a generally planar bone facing surface 48, and a second surface 50 which is disposed generally opposite the bone facing surface 48.

The guide element 22 has a height H (FIG. 3), measured in a direction from the bone facing surface 48 towards the second surface 50. The height increases in a direction from the first end 24 towards an intermediate section 52 of maximum height (which is the height H), the intermediate section disposed between the first and second ends 24 and 26. The height also increases in a direction from the second end 26 towards the intermediate section 52. The height $h_e$ (FIG. 3) of the guide element 22 at the first and second ends 24 and 26 is therefore less than the height H defined by the intermediate section 52. In a variation on the illustrated embodiment, the guide element need not necessarily have this height feature.

The saddle 46 is disposed within the intermediate section 52, and defines a space 54 (FIGS. 7 and 8) between the second surface 50 in the intermediate section and a maximum height extent 56 of the saddle 46, for receiving part of the loop 3 in order to couple the textile scaffold 1 to the guide element 22. Again, this feature of the saddle and the space may be optional and not included in other embodiments.

In the illustrated embodiment, the guide element 22 is formed by a metal injection moulding (MIM) process, although other suitable manufacturing techniques may be employed. A suitable MIM process involves forming a feedstock material comprising a metal and a plastics binder. The feedstock material is formed by mixing a powdered or granular metal material and a plastics binder material, and then forming the mixture into pellets. Suitable metal materials include Titanium and alloys thereof. Suitable plastics materials include thermoplastics materials. The pelletised feedstock material is heated to melt the plastics binder; injected into a mould to form a guide element of generally desired dimensions; cooled and ejected from the mould; subjected to a de-binding process in which a portion of the plastics binder is removed (e.g. by solvent extraction or catalytic decomposition); and the de-bounded element then sintered to decompose any remaining binder material and densify the guide element. Optionally the sintered guide element may be hot isostatically pressed (HIP'd) to achieve a desired density in the finished guide element. A finishing procedure may then be carried out which may include machining, surface finish enhancing and/or other suitable procedures.

In a variation on the illustrated embodiment, the guide element 22 is formed by a MIM process, but the generally planar bone facing surface 48, second opposed surface 50, guide element height and the space 54 defined between the second surface 50 and an intermediate section 56 are optional.

The support loop 3 is formed from a loosely structured fibre bundle of twisted yarn (not shown), and involves feeding the yarn from a supply through the support apertures 42 and 44 and along a guide path to form a basic loop; withdrawing further yarn from the supply simultaneously with applying movement of the basic loop along the guide path so as to apply successive loop turns to the basic loop and therefore form a progressively increasing loop core; and applying relative twists between the loop core and each successive loop turn so as to form a cohesive looped fibre bundle attached to the guide element 22. Full details of the method are disclosed in WO-99/47079, the disclosure of which is incorporated herein by way of reference.

The continuous loop 3 can optionally comprise UHM-WPE material, and may be entirely or partially formed from such a material. This may provide a continuous loop 3 of high strength and less bulk, compared to loops formed from materials that have conventionally been used, e.g. standard Polyester. An assembly comprising the guide element 22 and a continuous loop 3 comprising UHMWPE would therefore have a comparatively high strength, compared to prior assemblies having conventional guide elements and continuous loops.

The pulling element 34 is then attached to the guide element 22 by passing it through the pulling aperture 30, and tying it to form a pulling loop 35. The manipulating element 40 is similarly passed through the manipulating aperture 36, and tied to form a manipulating loop 41.

The textile scaffold 1 (with or without the graft 4) is then located through the loop 3 to complete the assembly 32. The assembly 32 is then drawn up through the tunnel portion 18 in the tibia 14 and through the tunnel portion 20 in the femur 12. This is achieved by pulling the guide element 22, trailing the loop 3 and attached textile scaffold 1, through the tunnel portions 18, 20 using the pulling element 34. The guide element 22 orients itself generally parallel to an axis of the bone tunnel 17 and, on emergence from the mouth 38 of the bone tunnel 20, the guide element 22 is manipulated to overlie the tunnel mouth using the manipulating element 40. The assembly 32 can then be pulled back so that portions of the bone facing surface 48 rest upon an outer surface 58 of the femur 12, and the textile scaffold 1 can then be tensioned and anchored by a suitable anchoring element such as an interference screw (not shown), inserted into a mouth 60 of the tunnel portion 18.

Further features of the guide element 22 will now be described in more detail.

The space 54 defined between the second surface 50 and the maximum extent 56 of the saddle 46 receives part of the support loop 3, as best shown in FIG. 10. The guide element 22 is effectively recessed in the intermediate section 52, and this restricts the extent to which the loop 3 protrudes beyond the second surface 50. This provides advantages including restricting the likelihood of the loop 3 suffering damage during passage along the bone tunnel 17, reducing the likelihood of the guide element 22 becoming lodged in the tunnels, and also enabling use of a loop of greater width than might otherwise be the case. The latter may be particularly advantageous because this may avoid a requirement to use higher strength, higher cost materials which has been done in the past, in an effort to provide a less bulky loop.

The saddle 46 is disposed substantially perpendicular to the longitudinal axis 28 of the guide element 22, on an axis 68 which is shown in FIG. 2. The saddle 46 has a surface 62 which defines the upper extent 56 of the saddle. As best shown in FIG. 7, the surface 62 is generally curved and is optionally semi-circular in cross-section, having a substantially constant radius of curvature. Alternatively however, the surface may have a planar upper or outer section and rounded, curved or radiused edges. An opposite (minimum) extent 64 of the saddle 46 is disposed in the plane of the bone facing surface 48, such that a portion 66 of the saddle 46 is generally planar. In a variation however a space may be provided between the bone facing surface 48 and the minimum extent 64 of the saddle 46.

The guide element 22 has a first sidewall 70 and a second sidewall 72 opposite the first. The side walls 70 and 72 are generally planar, and extend between the bone facing surface 48 and the second surface 50. The sidewalls 70 and 72 increase in height from the first and second ends 24 and 26 towards the intermediate section 52 of the guide element 22. The height of the guide element 22 is thus effectively determined by the heights of the sidewalls 70 and 72.

The intermediate section 52 extends part way along a length of the guide element 22, and is disposed substantially centrally along a length of the guide element. As best shown in FIG. 2, the guide element 22 is symmetrical about the line 68, which passes through a mid-point 74 of the guide element.

The second surface 50 forms an outer or upper surface of the guide element 22 (depending on factors including orientation), and is generally curved in a direction along the longitudinal axis 28. This provides a smooth transition from the lower height ends 24 and 26 (having the height $h_e$) towards the intermediate section (having the height H). This may facilitate passage of the guide element 22 along the bone tunnel 17. A radius of curvature of the second surface 50 increases in the directions from the first and second ends 24, 26 towards the intermediate section 52. The intermediate section 56 is of a constant height, so that the second surface 50 is flat (non-curved) in the intermediate section, viewed from the side. However, the entire second surface 50 may be curved, a radius of curvature being greatest in the intermediate section and smallest at the ends. If desired, the radius of curvature may be substantially constant.

Each of the support apertures 42 and 44 are generally quadrilateral in shape, and in particular generally square, when viewed in plan (or in a plane parallel to the bone facing surface 48). The guide element 22 defines first side surfaces 76 and second side surfaces 78 of the support apertures 42 and 44, and these side surfaces are disposed generally parallel to the longitudinal axis 28. The guide element 22 also defines first end surfaces 80 and second, opposite end surfaces 82 of the support apertures 42 and 44, the end surfaces being disposed substantially perpendicular to the longitudinal axis 28. Intersection zones or regions 83 are defined between the end surfaces 80, 82 and the side surfaces 76, 78 of each support aperture 42 and 44. The intersection regions 83 are curved, rounded or radiused, to restrict the likelihood of the loop 3 being damaged during use, through contact with the guide element 22.

The support apertures 42 and 44 also each comprise first openings 84 which open onto the bone facing surface 48, and second opposite openings 86 which open onto the second surface 50. Intersection zones or regions 88 are defined between the end surfaces 80 of the support apertures 42, 44 and the bone facing surface 48. Similarly, intersection zones or regions 90 are defined between the end surfaces 80 and the second surface 50. Intersection zones or regions 92 and 94 are also defined between the sidewalls 76, 78 and the bone facing surface 48/second surface 50, respectively. Again, the intersection regions 88, 90, 92 and 94 are curved, rounded or radiused to define a smooth transition. This again serves to reduce the likelihood of the loop 3 being damaged during use. The intersection regions 88 and 92 are of a larger dimension than the regions 90 and 94, to provide a smoother transition, which is particularly intended to restrict the likelihood of the loop 3 being damaged during passage of the guide element 22 along the bone tunnels 18 and 20, when the loop will come into contact with one of the intersection regions 88 (and possibly the region 92) for an extended period of time.

The guide element 22 also defines surfaces 95 of the pulling and manipulating apertures 30 and 36. The pulling and manipulating apertures 30 and 36 have first and second openings 96 and 98, which open respectively onto the bone facing surface 48 and the second surface 50. Intersection zones or regions 100 and 102 are defined between the surfaces 95 of the support apertures and the bone facing surface 48/second surface 50, respectively. The intersection regions 100, 102 are curved, rounded or radiused to restrict the likelihood of the pulling and manipulating elements 34, 40 being damaged during use, through contact with the guide element 22.

The various different apertures 30, 36, 40 and 42 are effectively defined by the saddle 46, as well as by two spaced bridges 104 and 106. The bridges 104, 106 are disposed substantially perpendicular to the longitudinal axis 28, and serve not only to strengthen the guide element 22, but also to space the pulling and manipulating elements 30, 34 and support loop 3 from one another.

Typically the height H of the guide element 22 in the intermediate section 56 is in the region of 2 mm, and the height $h_e$ at the ends 24 and 26 in the region of 1.0 to 1.1 mm. This provides a significant increase in stiffness of the guide element, when compared to a guide element having a consistent, conventional height of around 1.5 mm. This is achieved without hampering passage of the guide element 22 along the bone tunnel 17. Significant increases in strength are also achieved by manufacturing the guide element 22 in an MIM process. The guide element 22 of the present invention, having the above height features and manufactured in an MIM process, has been found in tests to be capable of supporting a load of 3000N applied through a (high strength, e.g. UHMWPE) support loop 3, compared to around 1500N for a conventional guide element of consistent, conventional height (~1.5 mm) and construction (non-MIM).

The space 54 defined between the surface 62 of the bridge 46 and the surface 50 is typically in the range of 0.5 mm, so that the bridge has a height of around 1.5 mm. This has been found to provide a good balance of recessing the loop 3 into the surface 50 and strength of the bridge.

Figure 11:
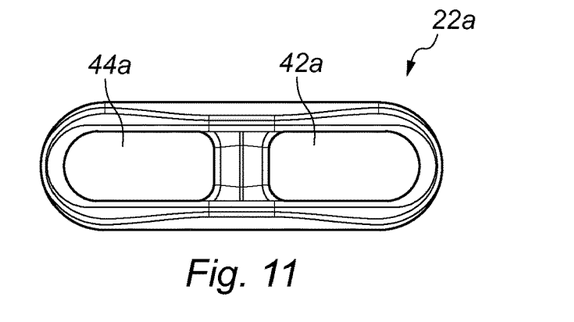
FIGS. 11 and 12 are plan and side views, respectively, of an elongate guide element for guiding an implant along a tunnel in a bone and for securing the implant within the tunnel, in accordance with another embodiment of the present invention.
Figure 12:
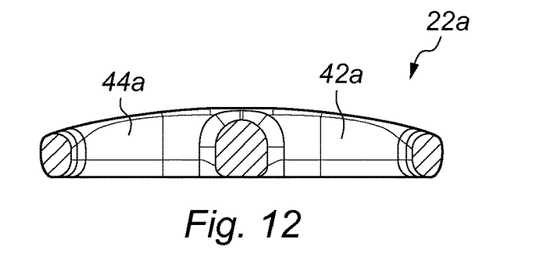

Turning now to FIGS. 11 and 12, there are shown plan and side views, respectively, of an elongate guide element in accordance with another embodiment of the present invention, the guide element indicated generally by reference numeral 22a. Like features of the guide element 22a with the guide element 22 of FIGS. 1B to 10 share the same reference numerals, with the addition of the suffix 'a'. Only the substantive differences between the guide elements 22a and 22 will be described herein.

In this embodiment, the guide element 22a comprises a pair of support apertures 42a, 44a each of which is adapted to receive one of the pulling element 34 and the manipulating element 40. Typically, one of the support apertures 42a and 44a will receive the pulling element 34, and the other one the manipulating element 40. The support apertures 42a and 44a are substantially elongate, typically in the form of slots, to accommodate part of the support loop 3, and part of one of the pulling and manipulating elements 34, 40. In this way, it is not necessary to provide dedicated apertures for the pulling and manipulating elements 34 and 40.

Figure 13:
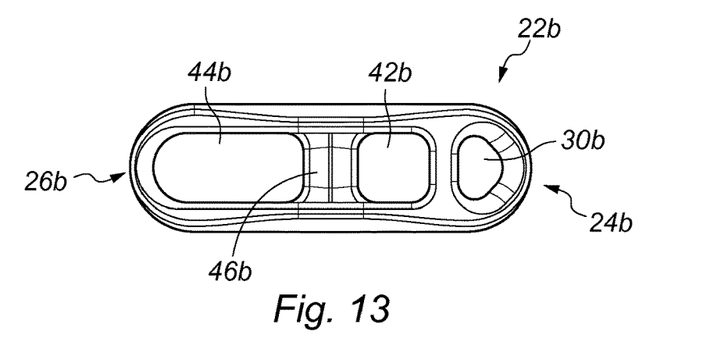
FIGS. 13 and 14 are plan and side views, respectively, of an elongate guide element for guiding an implant along a tunnel in a bone and for securing the implant within the tunnel, in accordance with a further embodiment of the present invention.
Figure 14:
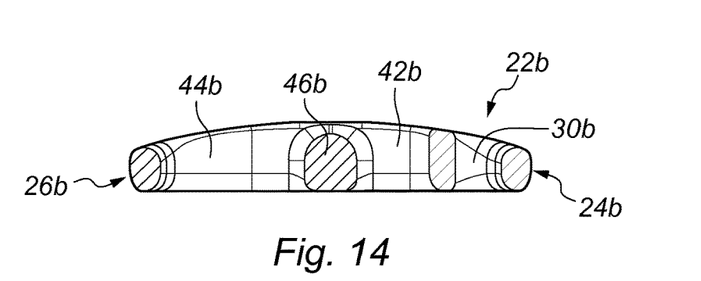

Turning now to FIGS. 13 and 14, there are shown plan and side views, respectively, of an elongate guide element in accordance with a further embodiment of the present invention, the guide element indicated generally by reference numeral 22b. Like features of the guide element 22b with the guide element 22 of FIGS. 1B to 10 share the same reference numerals, with the addition of the suffix 'b'. Only the substantive differences between the guide elements 22b and 22 will be described herein.

In this embodiment, the guide element 22b comprises a pair of support apertures 42b and 44b, and a further aperture 30b. The further aperture 30b is provided towards one of a first end 24b and a second end 26b of the guide element 22b, in this case, towards the first end. The further aperture 30b receives one of the pulling element 34 and the manipulating element 40 and, in this case, receives the pulling element.

The support aperture 44b receives part of said other one of the pulling and manipulating elements 34 and 40 and, in this case, receives the manipulating element. The support aperture 44b is substantially elongate, typically in the form of a slot, to accommodate part of the support loop 3, and part of the manipulating element 40. The support aperture 42b is disposed between a saddle 46b and the further aperture 30b, whilst the support aperture 44b is disposed between the saddle and the second end 26b of the guide element.

Various modifications may be made to the foregoing without departing from the spirit or scope of the present invention.

The support apertures, further aperture, pulling aperture and manipulating apertures shown in the enclosed drawings have particular shapes. However, it will be appreciated that these shapes may be varied if desired. In particular, whilst support apertures are shown which are generally quadrilateral-shape (being generally square or rectangular, optionally with rounded ends), the support apertures may have other shapes such as generally circular or elliptical, a rounded slot, or a combination of a rounded slot and a generally square end.

It will be obvious to those having skill in the art that many changes may be made to the details of the above-described embodiments without departing from the underlying principles of the invention. The scope of the present invention should, therefore, be determined only by the following claims.

The invention claimed is:

1. A one-piece elongate guide element for guiding an implant along a tunnel in a bone and for securing the implant within the tunnel, the one-piece guide element comprising:
a first end, a second end opposite the first end, and a main longitudinal axis extending between said ends;
a pair of support apertures for receiving a loop by which the implant can be coupled to the one-piece guide element, the support apertures being spaced apart in a direction along the main longitudinal axis;
a saddle extending in a direction transverse to the main longitudinal axis, one of the pair of support apertures being disposed between the saddle and the first end and the other between the saddle and the second end, in which the one-piece guide element is adapted to receive the loop so that the loop extends through one of the pair of support apertures, at least partly around the saddle and then through the other one of the pair of support apertures;
a generally planar bottom defining a bone facing surface; and
a second surface disposed opposite the bone facing surface;
wherein the one-piece guide element has a height, measured in a direction from the generally planar bottom towards the second surface, the height increasing from a first height defined by the first end towards an intermediate section of maximum height disposed between the first and second ends, and from a second height defined by the second end towards the intermediate section of maximum height; and
wherein the saddle defines a third height which is greater than each of the first height and the second height, the intermediate section comprises the saddle, and the third height is less than the maximum height so that a recess is defined in the second surface of which is adapted to receive part of the loop.

2. The one-piece guide element of claim 1, wherein the one-piece guide element is formed by a metal injection moulding (MIM) process.

3. The one-piece guide element of claim 1, wherein the maximum extent of the saddle is considered in the direction that the height of the one-piece guide element is measured.

4. The one-piece guide element of claim 1, wherein an opposite extent of the saddle is disposed in the plane of the generally planar bone facing surface.

5. The one-piece guide element of claim 1, wherein the saddle has a surface which defines the upper extent of the saddle, and in which said surface is curved in a direction along the longitudinal axis of the one-piece guide element.

6. The one-piece guide element of claim 1, wherein the one-piece guide element comprises a first side wall and a second side wall opposite the first side wall, the side walls extending between the bone facing surface and the second surface and increasing in height from the first and second ends towards the intermediate section.

7. The one-piece guide element of claim 1, wherein the one-piece guide element is symmetrical about a line which is perpendicular to the longitudinal axis and which passes through a midpoint of the one-piece guide element along a length thereof.

8. The one-piece guide element of claim 1, wherein the second surface is generally curved.

9. The one-piece guide element of claim 8, wherein the second surface is curved in a direction along the longitudinal axis of the one-piece guide element, a radius of curvature of the second surface increasing in the direction from the first end towards the intermediate section, and from the second end towards the intermediate section.

10. The one-piece guide element of claim 9, wherein the intermediate section is of a constant height, so that the second surface is flat in the intermediate section, viewed from the side.

11. The one-piece guide element of claim 1, wherein the guide element defines surfaces of the support apertures, and intersection regions between:
- the surfaces of the support apertures and the bone facing surface; and/or
- the surfaces of the support apertures and the second surface;
- wherein at least some of the intersection regions are rounded.

12. The one-piece guide element of claim 1, wherein each support aperture has a shape which is generally quadrilateral, when viewed in plan.

13. The one-piece guide element of claim 12, wherein the one-piece guide element defines:
- a first side surface of each support aperture and a second side surface opposite the first;
- a first end surface of each support aperture and a second end surface opposite the first, the first and second end surfaces disposed transverse to the longitudinal axis; and
- intersection regions between the end surfaces and the side surfaces, in which at least some of the intersection regions are rounded.

14. The one-piece guide element of claim 13, wherein the saddle defines end surfaces of each support aperture.

15. The one-piece guide element of claim 13, wherein each support aperture comprises a first opening which opens on to the bone facing surface and a second opening, opposite the first, which opens on to the second surface, and wherein the one-piece guide element defines intersection regions between:
- the end surfaces and the bone facing surface;
- the end surfaces and the second surface;
- the side surfaces and the bone facing surface; and/or
- the side surfaces and the second surface;
- and in which at least some of the intersection regions are rounded.

16. The one-piece guide element of claim 1, wherein the support apertures are each adapted to receive one of:
- a pulling element for pulling the guide element through the bone tunnel; and
- a manipulating element for manipulating the guide element to overlie a mouth of the bone tunnel on emergence therefrom.

17. The one-piece guide element of claim 1, further comprising a further aperture, provided towards one of the first and second ends, for receiving one of:
- a pulling element for pulling the guide element through the bone tunnel; and
- a manipulating element for manipulating the guide element to overlie a mouth of the bone tunnel on emergence therefrom.

18. The one-piece guide element of claim 17, wherein one of the support apertures is adapted to receive part of said other one of the pulling and manipulating elements.

19. The one-piece guide element of claim 17, further comprising at least one bridge extending transverse to the longitudinal axis.

20. The one-piece guide element of claim 1, wherein the one-piece guide element comprises:
- a pulling aperture provided towards one of the first and second ends, the pulling aperture shaped to receive a pulling element for pulling the one-piece guide element through the bone tunnel; and
- a manipulating aperture provided towards the other one of the first and second ends, the manipulating aperture shaped to receive a manipulating element for manipulating the one-piece guide element to overlie a mouth of the bone tunnel on emergence therefrom.

21. The one-piece guide element of claim 20, wherein one of the support apertures is disposed between the saddle and the pulling aperture, and the other between the saddle and the manipulating aperture.

22. The one-piece guide element of claim 20, wherein the pulling and manipulating apertures each comprise a first opening which opens on to the bone facing surface and a second opening, opposite the first, which opens on to the second surface.

23. The one-piece guide element of claim 22, wherein the one-piece guide element defines surfaces of the pulling and manipulating apertures, and intersection regions between:
- the surface of the pulling and manipulating apertures, and the bone facing surface; and/or
- the surfaces of the pulling and manipulating apertures, and the second surface;
- and in which at least some of the intersection regions are rounded.

24. An assembly for guiding an implant along a tunnel in a bone and for securing the implant within the tunnel, the assembly comprising:
- a one-piece elongate guide element for guiding an implant along a tunnel in a bone and for securing the implant within the tunnel; and
- a loop by which the implant can be coupled to the one-piece elongate guide element;
- wherein the one-piece elongate guide element comprises:
- a first end, a second end opposite the first end, and a main longitudinal axis extending between said ends;
- a pair of support apertures for receiving the loop by which the implant can be coupled to the one-piece elongate guide element, the support apertures being spaced apart in a direction along the main longitudinal axis;
- a saddle extending in a direction transverse to the main longitudinal axis, one of the pair of support apertures being disposed between the saddle and the first end and the other between the saddle and the second end, whereby, in use, the loop extends through one of the pair of support apertures, at least partly around the saddle and then through the other one of the pair of support apertures;
- a generally planar bottom defining a bone facing surface; and
- a second surface disposed opposite the bone facing surface;
- wherein the one-piece elongate guide element has a height, measured in a direction from the generally planar bottom towards the second surface, the height increasing from a first height defined by the first end towards an intermediate section of maximum height disposed between the first and second ends, and from a second height defined by the second end towards the intermediate section of maximum height;
- wherein the saddle defines a third height which is greater than each of the first height and the second height, the intermediate section comprises the saddle, and the third height is less than the maximum height so that a recess is defined in the second surface which is adapted to receive part of the loop; and
- wherein the loop comprises UHMWPE material.

* * * * *